United States Patent
Evans et al.

(10) Patent No.: US 8,771,708 B2
(45) Date of Patent: Jul. 8, 2014

(54) BIOLOGICALLY-ACTIVE RADIOLABELED CRY1FA AND RECEPTOR BINDING ASSAY METHODS

(75) Inventors: Steven L. Evans, Zionsville, IN (US); Jianquan Li, Zionsville, IN (US); Joel J. Sheets, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 79 days.

(21) Appl. No.: 13/327,842

(22) Filed: Dec. 16, 2011

(65) Prior Publication Data

US 2012/0156803 A1 Jun. 21, 2012

Related U.S. Application Data

(60) Provisional application No. 61/423,844, filed on Dec. 16, 2010.

(51) Int. Cl.
*A61K 39/07* (2006.01)

(52) U.S. Cl.
USPC ..... 424/246.1; 436/501; 530/350; 424/236.1; 424/9.6

(58) Field of Classification Search
None
See application file for complete search history.

(56) References Cited

U.S. PATENT DOCUMENTS

| 2005/0064386 A1 | 3/2005 | Adang et al. |
| 2010/0017914 A1 | 1/2010 | Hart et al. |

OTHER PUBLICATIONS

Palmer et al (Analytical Biochem. 253: 175-179. 1997).*
Kim et al Bioconjug Chem. Mar. 2008; 19(3): 786-791.*
Bravo, A. et al. "N-terminal Activation Is an Essential Early Step in the Mechanism of Action of the *Bacillus thuringiensis* Cry1Ac Insecticidal Toxin" *The Journal of Biological Chemistry*, Jul. 5, 2002, pp. 23985-23987, vol. 277, No. 27.
Choma, C. T. et al. "Unusual proteolysis of the protoxin and toxin from *Bacillus thuringiensis*" *Eur. J. Biochem.*, 1990, pp. 523-527, vol. 189.
De Maagd, R. A. et al. "Domain III of the *Bacillus thuringiensis* delta-endotoxin Cry1Ac is involved in binding to *Manduca sexta* brush border membranes and to its purified aminopeptidase N" *Molecular Microbiology*, 1999, pp. 463-471, vol. 31, No. 2.
De Maagd, R. A. et al. "Domain III substitution in *Bacillus thuringiensis* delta-endotoxin Cry1A(b) results in superior toxicity for *Spodoptera exigua* and altered membrane protein recognition" *Appl. Environ. Microbiol.*, 1996, pp. 1537-1543, vol. 62, No. 5.
Jurat-Fuentes, J. L. et al. "Altered Glycosylation of 63- and 68-Kilodalton Microvillar Proteins in *Heliothis virescens* Correlates with Reduced Cry1 Toxin Binding, Decreased Pore Formation, and Increased Resistance to *Bacillus thuringiensis* Cry1 Toxins" *Appl. Environ. Microbiol.*, Nov. 2002, pp. 5711-5717, vol. 68, No. 11.
Jurat-Fuentes, J. L. et al. "Importance of Cry1 δ-Endotoxin Domain II Loops for Binding Specificity in *Heliothis virescens* (L.)" *Applied and Environmental Microbiology*, Jan. 2001, pp. 323-329, vol. 67, No. 1.
Luo, K. et al. "Toxicity, Binding, and Permeability Analyses of Four *Bacillus thuringiensis* Cry1 δ-Endotoxins Using Brush Border Membrane Vesicles of *Spodoptera exigua* and *Spodoptera frugiperda*" *Appl. Environ. Microbiol*, Feb. 1999, pp. 457-464, vol. 65, No. 2.
Risk Assessment and Risk Management Plan, "Agronomic assessment and seed increase of GM cotton expressing insecticidal genes from *Bacillus thuringiensis*" Nov. 2003, pp. 1-145.
Written Opinion in International Application No. PCT/US2011/65322, Apr. 12, 2012, pp. 1-4.

* cited by examiner

*Primary Examiner* — Jennifer Graser
(74) *Attorney, Agent, or Firm* — Ronald S. Maciak; Saliwanchik, Lloyd & Eisenschenk

(57) ABSTRACT

Cysteine-specific radiolabeled Cry1Fa protein retains insecticidal activity against insect pests and binds to insect brush border membrane vesicles receptors in a saturable manner. The biologically-active radiolabeled Cry1Fa protein is useful in competitive binding assays with other Cry toxins.

2 Claims, 1 Drawing Sheet

Figure 1

**Bioassay of trypsin-truncated Cry1Fa and fluorescein-5-malemide labeled, trypsin-truncated Cry1Fa against *S. frugiperda* larvae**

Figure 2

Saturation Binding of radio-iodinated Cry1Fa core toxin protein to ECB BBMVs

BIOLOGICALLY-ACTIVE RADIOLABELED CRY1FA AND RECEPTOR BINDING ASSAY METHODS

CROSS-REFERENCE TO RELATED APPLICATION

This application claims the benefit of U.S. Provisional Application Ser. No. 61/423,844, filed Dec. 16, 2010, the disclosure of which is hereby incorporated by reference in its entirety, including all figures, tables and amino acid or nucleic acid sequences.

BACKGROUND OF THE INVENTION

The general field of the invention is the area of life sciences, particularly agricultural sciences and testing methods. Specifically, the field of the invention is the biochemistry and mode of action of *Bacillus thuringiensis* crystalline (Cry) endotoxins and their interactions with insect Cry toxin receptors.

Cry insecticidal proteins are endotoxins produced by *Bacillus thuringiensis* (Bt), a Gram positive bacterium found globally distributed in different soil types. Various classes of Cry proteins are selectively toxic against certain insect pests. The endotoxin is typically found in the form of a crystalline protein located in large inclusion bodies of the bacterium. Cry toxins have considerable sequence diversity (Crickmore et al., 1998; de Maagd et al., 2003), but the majority of the toxins that have activity against lepidopteran pests are 130 kDa protoxins having a three domain active core toxin structure (de Maagd et al., supra.).

The subject of the current invention relates to the Cry1Fa toxin, a three domain Cry protein. This toxin has demonstrated insecticidal activity against various lepidopteran insects, including *Spodoptera frugiperda* (J. E. Smith) (fall armyworm) and *Ostrinia nubilalis* (Hübner) (European corn borer), which are two of the most economically important insect pests of maize. Cry1Fa is the toxin component of two USDA deregulated transgenic plant incorporated pesticides know as event TC1507 in maize (HERCULEX®) and event 281-24-236 in cotton (WIDESTRIKE®).

Cry1Fa full-length holotoxin protein, like other three-domain Cry toxins, requires proteolytic cleavage at both the N-terminus and the C-terminus ends for activation of its insecticidal activity. The midguts of lepidopteran insects contain a variety of trypsin and chymotrypsin-like proteases that process the full length holotoxin to a core toxin structure having a size of approximately 68 kDa (Christeller et al., 1992; Gatehouse et al., 1997; Bernardi et al., 1996). The processing involves removal of approximately 28 amino acids from the N-terminus and approximately 530 amino acids from the C-terminus (protoxin segment), and the resulting core toxin segment is released and binds to specific receptors located within the insect gut.

Insects can develop resistance to the activity of Cry protein toxins through changes in midgut localized receptors that bind the Cry protein core toxin (Heckel et al., 2007; Van Rie et al., 1990b). Further, other mechanisms of resistance development have been documented, including: reduced activation of the protoxin, changes in the number of Cry receptors in the insect midgut, and the loss of the ability to respond to the toxin by formation of membrane pores that contribute to insect mortality (see Griffitts and Aroian, 2005; and Van Rie et al., 1990b).

Prior to this invention, studies to characterize the binding of Cry1Fa core toxin protein to different insect receptors have not been reported. The reason being was that traditional radio-labeling methods involving oxidized iodine isotopes reacting with tyrosine residues in the Cry1Fa toxin produced radiolabeled core toxin protein that lost its ability to bind to receptors in brush border membrane vesicles (BBMVs) prepared from midguts of *Spodoptera exigua* and *Spodoptera frugiperda* (Luo et al., 1999). Further, it was found that traditionally radiolabeled Cry1Fa core toxin protein lost its insecticidal activity and was inactive in diet bioassay's against these *Spodoptera* species. Other methods of protein labeling such as fluorescent labeling, and other methods to measure ligand-receptor binding such as isothermal calorimetry, have been attempted, but have been found to be either too insensitive, or the optical methods too difficult to use due to the particulate properties of insect BBMVs.

Palmer et al. (1997) described an indirect method of radioactive labeling of proteins specifically at cysteine residues. In this method, an intermediate compound, fluorescein-5-maleimide, is first reacted with radio-iodine, then the radiolabeled fluorescein-5-maleimide is used to chemically modify the protein at available cysteine residues. This invention describes the use of the highly specific Palmer et al. method to radiolabel Cry1Fa protein by targeting a single cysteine residue (C205) located in Domain 1 of the Cry1Fa core toxin.

It was most surprising to find that the introduction of this stearically cumbersome radiolabeled 5-maleimide into the Cry1Fa core toxin protein prepared by this method did not result in a loss of binding to its receptor or cause toxin inactivation. As a result, this non-traditionally radiolabeled Cry1Fa core toxin maintained sufficient tertiary protein structure to retain both its insecticidal activity and its ability to bind specifically to receptors in BBMV preparations from a variety of insects.

The non-traditionally radiolabeled Cry1Fa protein was found to bind to receptors in a saturable manner, and was used in a competitive binding assay to determine if other Cry toxins compete with its binding. Using this assay it was demonstrated that field resistance to Cry1Fa toxin that developed in a population of *S. frugiperda* collected in Puerto Rico is due to the loss of the ability of receptors in BBMVs of these insects to bind Cry1Fa core toxin protein.

BRIEF DESCRIPTION OF THE FIGURES

FIG. 1 is a bioassay of trypsin-truncated Cry1Fa and fluorescein-5-malemide labeled, trypsin-truncated Cry1Fa against *S. frugiperda* larvae. The figure summarizes the results of insect diet bioassays with *Spodoptera frugiperda* neonate larvae using iodinated (nonradioactive) Cry1Fa core toxin protein prepared by the method of the current invention.

FIG. 2 shows saturation binding curves of radio-iodinated Cry1Fa core toxin protein to European Corn Borer (ECB) BBMVs. The figure depicts the saturation binding of radio-iodinated Cry1Fa core toxin protein prepared by the method of the current invention to BBMVs prepared from *Ostrinia nubilalis* larval midguts.

BRIEF DESCRIPTION OF THE SEQUENCE IDENTIFICATIONS

SEQ ID NO:1 is the synthetic DNA sequence encoding Cry1Fa holotoxin.

SEQ ID NO:2 is the Cry1Fa holotoxin.

DETAILED DESCRIPTION OF THE INVENTION

Three structural domains of the Cry1Fa protein are located within the "tryptic core" that is resistant to further trypsin digestion. Domain I is composed of seven α-helices which are believed to insert into the membrane of the insect midgut and form a pore-like structure (Ballester et al., 1999). Domain II consists of three antiparallel β-sheets, and Domain III forms a β-sandwich structure (Pigott and Ellar, 2007). Exposed regions of domains II and III are believed to interact with specific receptors located on the luminal surface of the insect midgut and bind tightly to these receptors (Bravo et al., 2007; de Maagd et al., 1996; de Maagd et al., 1999; Gomez et al., 2006; Herrero et al., 2004; Lee et al., 1999). Binding of the toxin to a receptor is a necessary requirement for insecticidal activity, and provides the specificity and selectivity of the toxins (Pigott and Ellar, 2007; Rausell et al., 2004). The specificity of activity of different Cry proteins against different insect species has been shown to be related in part to differences in receptors found in different insects (Gomez et al., 2003; Gomez et al., 2007; Van Rie et al., 1990a).

Quantitative biochemical assays provide a means to measure the interaction of Cry toxins with receptor proteins found in insect midguts. In saturation type binding assays, the labeled Cry toxin protein (ligand) is incubated in buffer solutions that promote the binding of the Cry toxin protein to an insect receptor protein. In one embodiment of a saturation binding assay, a fixed amount of insect receptor protein (commonly brush border membrane vesicles prepared from insect midguts) is mixed (in separate tubes) with increasing amounts of iodinated Cry toxin protein, and allowed to react for a set amount of time. Unbound Cry protein (that is, not bound to an insect receptor protein) is separated from bound protein by one of various methods, and the amount of radioactivity in the bound protein fraction provides an indication of the amount of Cry protein bound to the insect receptor. One skilled in the field of biochemistry will realize that an observation of little or no bound radioactivity will indicate the lack of a receptor for the particular Cry toxin being studied in the insect species from which the receptor preparation was made.

A second embodiment of a binding assay is a competitive assay. In a competitive binding assay, the radioactive Cry toxin protein is mixed with an excess of a second, nonradioactive Cry protein, and the Cry proteins are allowed to bind under standard conditions to insect receptor proteins. If the second, non radioactive Cry toxin protein is able to compete with the radioactive Cry toxin protein for binding to the insect receptor, then the radioactive protein will be displaced from the receptor binding site, and little radioactivity will be recovered in the bound state. If the nonradioactive and the radioactive Cry toxin proteins bind to different insect receptor proteins, then they will not compete with one another in binding to the same insect receptor protein. In this instance, the amount of radioactivity recovered in the bound protein fraction will be the same, or nearly the same, as when the nonradioactive second Cry toxin protein was not present in the binding reaction. Various methods are available to quantify the amount of radioactivity in the bound protein fraction.

Competitive binding assays using $^{125}$I-Cry1Fa core toxin protein and either nonradioactive Cry1Fa core toxin protein (control reaction) or Cry1Ab core toxin protein demonstrated that both of the nonradioactive core Cry toxin proteins were able to displace the labeled Cry1Fa core toxin from its receptor site in BBMV's from *S. frugiperda*. By contrast, the competitive binding assay demonstrated that that Cry1Ca core toxin protein did not compete with Cry1Fa core toxin binding. The results of these binding assays demonstrate that the insect resistance to Cry1Fa toxin observed in field studies in a population of *S. frugiperda* collected in Puerto Rico can be explained by the inability of receptors in brush border membrane vesicles from these insects to bind Cry1Fa core toxin.

All patents, patent applications, provisional applications, and publications referred to or cited herein are incorporated by reference in their entirety to the extent they are not inconsistent with the explicit teachings of this specification.

Nucleic acid sequences are presented in the standard 5' to 3' direction, and protein sequences are presented in the standard amino (N) terminal to carboxy (C) terminal direction.

Unless specifically indicated or implied, the terms "a", "an", and "the" signify "at least one" as used herein.

Following are examples which illustrate procedures for practicing the invention. These examples should not be construed as limiting. All percentages are by weight and all solvent mixture proportions are by volume unless otherwise noted. All temperatures are in degrees Celsius.

EXAMPLE 1

Construction of Expression Plasmids Encoding Cry1Fa Toxin Protein and Expression in Bacterial Hosts Standard cloning methods (as provided by, for example, Sambrook et al., (1989) and Ausubel et al., (1997), and updates thereof) were used in the construction of pDAB1817, a *Pseudomonas fluorescens* (Pf) expression plasmid engineered to produce a chimeric toxin protein (herein referred to as Cry1Fa toxin; SEQ ID NO:2) comprised of a Cry1Fa core toxin segment (amino acids 1 to 603) and a Cry1Ab protoxin segment (amino acids 604 to 1148), encoded by a plant-optimized coding sequence (CDS; SEQ ID NO:1).

pDAB1817 is derived from pMYC1803 (U.S. Pat. No. 7,338,794). The basic cloning strategy entailed ligating a DNA fragment, flanked by SpeI and KpnI restriction enzyme recognition sites and containing the Cry1Fa toxin CDS, to the large fragment of pMYC1803 prepared by cleaving pMYC1803 DNA with SpeI and KpnI restriction enzymes. Plasmid pMYC1803 is a medium copy plasmid derived from the RSF1010-based plasmid pTJS260 (see U.S. Pat. No. 5,169,760), and carries a regulated tetracycline resistance marker and the replication and mobilization loci from the RSF1010 plasmid. By this means, the Cry1Fa toxin CDS was placed under the expression control of the Ptac promoter and the rrnBT1T2 terminator from plasmid pKK223-3 (PL Pharmacia, Milwaukee, Wis.). The expression plasmid pDAB1817 was transformed by electroporation into *P. fluorescens* strain MB217 (a derivative of strain MB101; *P. fluorescens* biovar I), with selection for resistance to tetracycline. Recombinant colonies were identified by restriction digestion of miniprep plasmid DNA.

Growth and Expression Analysis in Fermentors: Production of Cry1Fa toxin protein for biochemical manipulation and insect bioassay was accomplished by fermentor-grown *P. fluorescens* expression strain isolate DR1649. A seed culture was grown 20 hours (final Optical Density at 600 nm=14) at 32° in a shake flask containing 600 mL of Ps20 medium supplemented with 15 µg/mL tetracycline, and was used to inoculate 6.6 L of DGMp2.2 medium with tetracycline in a 20 L fermentor tank (New Brunswick Scientific BioFlo 4500, Edison, N.J.). Fermentation was carried out at 32° with agitation at 200 to 1000 rpm. Details of the microbiological manipulations for *P. fluorescens* are available in Squires et al. (2004), US Patent Application No. 20060008877, U.S. Pat. No. 7,681,799, US Patent Application No. 20080058262, and Huang et al. (2007), incorporated herein by reference. Glycerol was batch-fed periodically at 10 gm/L in response to dissolved oxygen concentration. Expression of the Cry1Fa toxin CDS via the Ptac promoter was induced by addition of isopropyl-β-D-1-thiogalactopyranoside (IPTG). Cultures were monitored throughout the post induction fermentation time to determine cell density, the level of target gene expression, and other parameters. For SDS-PAGE (sodium dodecyl sulfate polyacrylamide gel electrophoresis) and immunoblot analyses, aliquots of 0.1 mL of whole fermentation broth were frozen for subsequent analysis. At the final time point at 48 hours after IPTG induction (Optical Density at 600 nm=222; final culture volume=13.5 L), cells from 4 L of culture were harvested by centrifugation at 10000×g for 90 min. The cell pellets were frozen at −20° or −80° for further processing.

SDS-PAGE Analysis of fermentation samples: Frozen fermentor cell broths (0.1 mL) were diluted in chilled water by 5 fold and 200 μL were sonicated in ice for 10 minutes using a Branson 250 Sonifier (Branson Ultrasonics, Danbury Conn.) using a ⅛ inch diameter micro tip with a constant output of 20 units. The lysates were centrifuged at 14000 rpm for 20 minutes (4°) and the supernatants removed (soluble fraction). The pellets were then resuspended in 200 μL of phosphate buffered saline (PBS; 11.9 mM $Na_2HPO_4$, 137 mM NaCl, 2.7 mM KCl, pH7.4; Sigma-Aldrich, St. Louis, Mo.). Further dilutions of both the soluble and insoluble fractions of an equivalent of up to 20-fold of the original fermentation broth were performed in PBS. These fractions were then mixed 1:1 with Laemmli sample buffer (Bio-Rad Inc., Hercules, Calif.) containing 5% β-mercaptoethanol and boiled for 5 minutes prior to loading 10 μL to 20 μL on a Criterion 10% Bis-Tris gel with MOPS buffer (Bio-Rad Inc.). Gels were stained with Simply Blue SafeStain™ (Invitrogen, Carlsbad, Calif.) according to the manufacturer's protocol.

Immunoblotting: Standard biochemical methods (as provided by, for example, Sambrook et al., (1989) and Ausubel et al., (1997), and updates thereof) were used for protein isolations and immunoblot analyses. Samples were prepared and proteins were separated by electrophoresis through NuPAGE 4-12% Bis-Tris gels in MES running buffer according to the manufacturer's suggested protocol for denaturing electrophoresis (Invitrogen). Proteins were transferred onto nitrocellulose membrane for 80 min. at 30 V in NuPAGE transfer buffer. Blots were blocked for 1 hour at room temperature in 5% milk/PBST (PBS with 0.05% Tween-20) and then probed with primary antibody (specific for Cry1Fa core toxin segment) and then secondary antibodies for one hour each at room temperature in blocking solution, with rinsing in between each antibody for 15 minutes in PBST. Development of blots was done using Pierce's ECL Western blotting substrate according the manufacturer's protocol (Thermo Fisher Scientific, Rockford, Ill.).

EXAMPLE 2

Purification of Cry1Fa Core Toxin Protein from *Pseudomonas*-Produced Inclusion Bodies Inclusion body preparations: Protein inclusion bodies (IB) were prepared from *P. fluorescens* DR1649 cells that contained insoluble Cry1Fa toxin protein, as demonstrated by SDS-PAGE and MALDI-MS (Matrix Assisted Laser Desorption/Ionization Mass Spectrometry). A MALDI-R (Reflectron) mass spectrometer from Micromass (Milford, Mass.) was used to measure peptide masses in accordance with the manufacturer's prescribed methods and recommendations. Frozen cell pellets were thawed in a room temperature water bath. The cells were resuspended to 10% w/v in lysis buffer (50 mM Tris HCl, pH7.5; 200 mM NaCl; 5% Glycerol; 2 mM EDTA disodium salt (Ethylenediaminetetraacetic acid); 0.5% Triton X-100; and 1 mM DTT (dithiothreitol—added just prior to use)). 25 mL of protease inhibitor cocktail (Sigma-Aldrich) was added for every 100 gm of cell paste treated. The slurry was passed twice through a Microfluidics Microfluidizer at 12000+ psi (Microfluidics Intern. Corp., Newton, Mass.). The lysate was centrifuged at 18000×g at 4° for 30 min, and the supernatant was retained. The inclusion pellet was washed in lysis buffer without protease inhibitor cocktail until no bacterial odor remained (usually 2 or 3 washes), by gently homogenizing using a spatula or mechanical mixer (to about 10% w/v solids) and centrifuging as described. The resultant supernatants and final pellet were retained and stored at −20°. Small aliquots of each sample were taken and stored in a microcentrifuge tube for SDS-PAGE analysis. The inclusion body preparation pellets were then freeze-dried using a Virtis Advantage freeze dryer (Viopharma Process Systems LTD, Winchester, UK) at ambient shelf temperature and a maximum vacuum drawn for 2 days. The resulting powders were then stored at −20° until analyzed.

SDS-PAGE analysis and quantitation of IB preparations: Twenty-five mg of IB pellet were resuspended in 1 mL of HTS buffer (20 mM Tris HCL, pH7.5; 50 mM NaCl; 5% v/v glycerol, 10 mM EDTA disodium salt; 0.5% v/v Triton X-100) and sonicated as above for 1 minute on ice. The resuspended samples were then diluted 1:1 in Laemmli sample buffer containing 0.2 M DTT. The samples were then diluted 10× and 20× with Laemmli sample buffer without DTT and 10 μL were loaded onto a Criterion 18 well 10% Bis-Tris gel (Bio-Rad Inc.) run with 1× NuPAGE MES buffer (Invitrogen). Gels were run for 5 min at 100V and then 45 min at 200V. Gels were rinsed and washed in water for 20 min and stained with Simply Blue SafeStain™. Quantification of target bands was done by comparing densitometric values for the bands against a series of Bovine Serum Albumin (BSA) standard samples run on the same gel, and scanned to generate a densitometric standard curve.

Truncation and purification of Cry1Fa core toxin protein: Purified inclusion bodies were washed with sterile water, then solubilized in 20 mM CAPS, pH11 (3-(cyclohexamino)1-propanesulfonic acid) containing 10 mM DTT by rocking the protein solution for 1 hr at room temperature. After removing insoluble material by centrifugation (30000×g for 30 min at 4°), trypsin treated with 0.5% (w/v) tosyl phenylalanyl chloromethyl ketone (TPCK) (Sigma-Aldrich) was added to the supernatant. This solution was incubated with mixing for 1 hr at room temperature, filtered and concentrated 5-fold using an Amicon Ultra-15 regenerated cellulose centrifugal filter device (30000 Molecular Weight Cutoff; Millipore), then loaded onto a Pharmacia Mono Q 1010 column equilibrated with 20 mM CAPS pH10.5. After washing the loaded column with 2 column volumes of buffer, the truncated toxin protein was eluted using a linear gradient of 0 to 0.5 M NaCl in 20 mM CAPS pH10.5 in 15 column volumes at a flow rate of 1.0 mL/min. Purified trypsin-truncated Cry1Fa core toxin eluted at about 0.2 M to 0.3 M NaCl. The purity of the proteins was checked by SDS-PAGE with visualization using Coomassie brilliant blue dye (below). In some cases, the combined fractions of the purified toxin were concentrated and loaded onto a Superose 6 column (1.6 cm dia., 60 cm long; GE Healthcare Life Sciences), and further purified by size exclusion chromatography. Fractions comprising a single peak corresponding to the monomeric size of the truncated core toxin (ca. 68 kDa) were combined and concentrated, resulting in a preparation that was greater than 95% homogeneous for a protein having a molecular weight of about 68 kDa, as judged by SDS-PAGE.

SDS-PAGE analysis of purified Cry1Fa core toxin: SDS-PAGE analysis of trypsin truncated Cry1Fa toxin protein was conducted under reducing and denaturing conditions by the method of Laemmli (as per Sambrook et al., supra). Reduction of the proteins was achieved using 5% β-mercaptoethanol, and heat denaturation was performed at 90° for 5 minutes in the presence of 2% SDS. Proteins were loaded into wells of a 4% to 20% Tris-glycine polyacrylamide gel (Invitrogen) and separated at 200 volts for 60 minutes. Protein bands were stained with Coomassie Brilliant Blue R-250 (Bio-Rad) for one hour, and then destained with a solution of 5% methanol in 7% acetic acid in the presence of cellulose sponges. The gels were imaged and analyzed using a Bio-Rad Fluro-S Multi Imager™ with Quantity One™ imaging software. Relative molecular weights of the protein bands were determined by including a sample of BenchMark™ Protein Ladder (Life Technologies, Rockville, Md.) or See Blue™ prestained molecular weight marker (Invitrogen) in one well of the gel.

EXAMPLE 3

Preparation of Specifically Radio-Iodinated Cry1Fa Core Toxin Protein

Iodination of Cry1Fa core toxin protein: Previous work demonstrated that iodination of Cry1Fa toxin protein destroyed the capacity of the iodinated protein to bind to its receptor(s) in insect brush border membrane vesicles (BBMVs), as well as the insect toxicity of the protein (Luo et al., 1999). In that study, Cry1Fa toxin protein was radio-iodinated using a standard iodination bead method (Pierce Iodination Beads; Thermo Fisher Scientific), and binding studies revealed that the protein had lost all of its ability for specific binding to receptor(s) in BBMVs from S. exigua and S. frugiperda. Further, when non-radiolabeled NaI was used to iodinate Cry1Fa toxin protein employing the Iodination Bead method, the iodinated Cry1Fa was found to have lost its insecticidal activity against Spodoptera larvae in diet bioassays.

Iodination of proteins by Iodination Bead protocols takes place at positions ortho to the hydroxyl group on tyrosine; mono- or di-substitution can occur. Thus, the positions of iodination depend on the placement of tyrosine residues within the subject protein, and multiple iodinations may have the consequence of disruption of the protein's structure and/or function. It is noted that the Cry1Fa core toxin segment comprises 20 tyrosine residues, which may serve as iodination targets.

This example teaches an alternative method for labeling the Cry1Fa core toxin protein with radioactive iodine. Subsequent Examples teach that the radio-labeled core toxin protein binds to insect BBMVs, and that iodinated Cry1Fa core toxin protein is active in insect diet bioassays. Further, these Examples teach that trypsin truncated Cry1Fa core toxin protein can be specifically fluorescently labeled at the cysteine corresponding to the C205 residue of the Cry1Fa toxin protein using fluorescein-5-maleimide, and that the fluorescently labeled protein is biologically active, causing insect mortality at dosages equal to those of nonlabeled, trypsin truncated Cry1Fa core toxin.

The Cry1Fa core toxin segment contains three cysteine amino acid residues, at positions 9, 14, and 205. Truncation of the protein by trypsin treatment removes C9 and C14, providing a core toxin segment that retains the cysteine corresponding to the C205 residue. Palmer et al. (1997) demonstrated that the phenyl rings of fluorescein-5-maleimide can be radio-iodinated and then reacted with proteins that contain sulfhydryl groups (e.g. as provided by free cysteine residues), resulting in alkylation of the free cysteines in the protein, and thus providing a radioactively labeled protein. The trypsin-truncated Cry1Fa core toxin contains a single cysteine residue at the position corresponding to C205, and thus provides a substrate for alkylation and radiolabeling of the protein at a single (specific) site.

Fluorescein-5-maleimide (F5-M) was dissolved to 10 mM in DMSO (Dimethyl Sulfoxide), then diluted to 1 mM in phosphate buffered saline (PBS; 20 mM sodium phosphate, 0.15 M NaCl, pH7.5), as determined by the molar extinction coefficient of F 5-M (68,000 $M^{-1}cm^{-1}$). To a 70 μL solution of PBS containing two Pierce Iodination Beads (Thermo Fisher Scientific), 0.5 mCi of $Na^{125}I$ was added behind lead shielding. (An analogous procedure was performed using non-radioactive NaI to prepare (iodinated, non radioactive) fluorescently labeled Cry1Fa core toxin protein.) The solution was allowed to mix at room temperature for 5 min, then 10 μL of the 1 mM F 5-M solution were added. After reacting for 10 min, the solution was removed from the iodination by pipetting and 2 μg of highly purified trypsin-truncated Cry1Fa core toxin protein in PBS were added to the solution. The protein was incubated at 4° with the iodinated F 5-M solution for 48 hrs, when the reaction was terminated by adding β-mercaptoethanol to 14 mM final concentration. The reaction mixture was added to a Zebra™ spin column (Invitrogen) equilibrated in 20 mM CAPS, 150 mM KCl, pH9, and centrifuged at 1500×g for 2 min to separate non-reacted iodinated dye from the protein. The $^{125}I$ radiolabeled fluorescein-Cry1Fa core toxin protein was counted in a gamma counter to determine its specific radioactivity, assuming 80% recovery of the input toxin protein.

The specific activity of the radiolabeled Cry1Fa core toxin protein was approximately 1.1 μCi/μg protein. This specific activity was low compared to typical expected levels of labeling of similarly-sized proteins using the Iodination Bead procedure. This is presumably due to a single site of labeling (corresponding to C205), and to the (possibly) relative inaccessibility of that site, which is presumed to be located deep within Domain I of the core toxin segment (based upon localization using a comparison crystal structure of the Cry1Aa protein).

The radiolabeled protein was also characterized by SDS-PAGE and visualized by phosphor-imaging to validate that the radioactivity measured was covalently associated with the Cry1Fa core toxin protein. Radio-purity of the radio-iodinated Cry1Fa core toxin protein (and subsequent detection of Cry1Fa bound to its BBMV receptor) was determined by SDS-PAGE, phosphor-imaging and gamma counting. Coomassie stained SDS-PAGE gels were imaged by wrapping them in Mylar™ film (12 μm thick), and exposing them under a Molecular Dynamics (Sunnyvale, Calif.) storage phosphor screen (35 cm×43 cm) for 1 hour. The plates were developed using a Molecular Dynamics Storm 820 phosphor-imager and the image analyzed using ImageQuant™ software. The radioactive band along with areas immediately above and below the band were cut from the gel using a razor blade and counted in a gamma counter. Radioactivity was detected in the Cry1Fa core toxin protein band and in areas below the band. No radioactivity was detected in the gel region above the Cry1Fa core toxin protein band. Some radioactivity was detectable in the gel region below the Cry1Fa core toxin protein band (i.e. fragments smaller than the Cry1Fa core toxin protein). These radioactive contaminants likely represent degradation products of the Cry1Fa core toxin protein.

Fluorescently labeled (non-radioactive, iodinated) Cry1Fa core toxin protein thus prepared was used in insect diet feeding bioassays to demonstrate that insect toxicity had not been affected, and radio-iodinated (fluorescently labeled) Cry1Fa core toxin protein was used in binding studies with BBMV preparations to demonstrate that receptor binding activities had not been affected.

EXAMPLE 4

Insect Diet Feeding Bioassays

Trypsin-truncated Cry1Fa core toxin proteins, either non-radioactive iodine fluorescein-5-maleimide labeled, or unlabeled, were individually tested for their insecticidal activity in a top load diet bioassay against larvae of Spodoptera frugiperda (fall armyworm; FAW) Larvae of FAW were hatched from eggs obtained from a colony maintained by a commercial insectary (Benzon Research Inc., Carlisle, Pa.).

The bioassays were conducted in 128-well plastic trays specifically designed for insect bioassays (C-D International, Pitman, N.J.). Each well contained 0.5 mL of Multi-species Lepidoptera diet (Southland Products, Lake Village, Ariz.). A 40 µL aliquot of the purified Cry1Fa core toxin protein, diluted to various concentrations in 10 mM CAPS, pH10.5, or 40 µL of a control solution, were delivered by pipette onto the diet surface of each well (26.7 µL/cm$^2$). Sixteen wells were tested per sample. The negative control was a CAPS buffer solution blank containing no protein. Positive controls included preparations of full length Cry1Fa toxin. The treated trays were held in a fume hood until the liquid on the diet surface had evaporated or was absorbed into the diet. Diet concentrations of the Cry1F toxin proteins were calculated as the amount (ng) of Cry1F toxin protein per square centimeter of surface area in the well (1.5 cm$^2$).

Within a few hours of eclosion, individual larvae were picked up with a moistened camel hair brush and deposited on the treated diet, one larva per well. The infested wells were then sealed with adhesive sheets of clear plastic that are vented to allow gas exchange (C-D International, Pitman, N.J.). Bioassay trays were held under controlled environmental conditions (28°, about 40% Relative Humidity, 16:8 (Light:Dark)) for 5 days, after which time the total number of insects exposed to each protein sample, the number of dead insects, and the weight of surviving insects were recorded. Percent mortality and percent growth inhibition were calculated for each treatment. Growth inhibition (GI) was calculated as follows:

$$GI=[1-(TWIT/TNIT)/(TWIBC/TNIBC)]$$

where TWIT is the Total Weight of Insects in the Treatment,

TNIT is the Total Number of Insects in the Treatment

TWIBC is the Total Weight of Insects in the Background Check (Buffer control), and TNIBC is the Total. Number of Insects in the Background Check (Buffer control).

The $GI_{50}$ was determined to be the concentration of Cry1Fa toxin protein in the diet at which the GI value was 50%; i.e. the growth of the insects on Cry1Fa-containing diet was only half that of the insects on diet with no Cry1Fa protein, as calculated above. The $LC_{50}$ (50% Lethal Concentration; calculated as the concentration of Cry1Fa toxin protein in the diet at which 50% of test insects were killed) was not determined, as very little mortality was observed during the 5 day experimental period. Statistical analysis (One-way ANOVA) is done using JMP software (SAS, Cary, N.C.).

The labeled and non-labeled Cry1Fa core toxin proteins were approximately equally active at inhibiting growth of S. frugiperda larvae, causing fifty percent growth inhibition at concentrations between 33 ng/cm$^2$ and 100 ng/cm$^2$ (FIG. 1). This result shows that labeling of trypsin truncated Cry1Fa core toxin protein with iodinated fluorescein-5-maleimide does not result in loss of insecticidal activity.

EXAMPLE 5

Preparation of Brush Border Membrane Vesicles (BBMVs)

Preparation of Solubilized BBMVs: Last instar larvae of S. frugiperda and Ostrinia nubilalis (European corn borer) were held without food overnight and then dissected after chilling on ice for 15 minutes. The midgut tissue was removed from the body cavity, leaving behind the hindgut attached to the integument. The midgut was placed in 9× volume of ice cold homogenization buffer (17 mM Tris base, pH7.5, 300 mM mannitol, and 5 mM EGTA (Ethylene glycol tetraacetic acid)), supplemented with Protease Inhibitor Cocktail (Sigma-Aldrich P-2714) diluted as recommended by the supplier. The final concentration of cocktail components (in µM) were AEBSF (500), EDTA (250), Bestatin (32), E-64 (0.35), Leupeptin (0.25), and Aprotinin (0.075). The tissue was homogenized with 15 strokes of a glass tissue homogenizer. BBMVs were prepared by the $MgCl_2$ precipitation method of Wolfersberger (1993). Briefly, an equal volume of a 24 mM $MgCl_2$ solution was mixed with the midgut homogenate, stirred for 5 minutes and allowed to stand on ice for 20 min. The solution was centrifuged at 2500×g for 15 min at 4°. The supernatant was saved and the pellet suspended into 0.5× volume of homogenization buffer and centrifuged again. The two supernatants were combined, centrifuged at 27000×g for 30 min at 4° to form the BBMV fraction. The pellet was suspended into BBMV Storage Buffer (10 mM HEPES pH7.4 (4-(2-hydroxyethyl)-1-piperazineethanesulfonic acid), 130 mM KCl, 10% glycerol) to a concentration of about 3 mg/mL protein. Protein concentration was determined by using the Bradford method with BSA as the standard (Bradford, 1976). The leucine-p-nitroanilide assay for aminopeptidase N determination was made prior to freezing the samples using a Sigma-Aldrich assay kit following the manufacturer's instructions. The specific activity of this marker enzyme in the BBMV fraction typically increased 7-fold compared to that found in the midgut homogenate fraction. The BBMV preparations were dispensed into 250 µL samples, flash frozen in liquid nitrogen, and stored at −80°.

EXAMPLE 6

Iodinated Cry1Fa Core Toxin Protein Binding Assays to BBMVs

Binding of $^{125}$I-Cry1Fa core toxin protein to BBMVs: To determine the optimal amount of BBMV protein to use in competitive binding assays, a saturation curve was generated. $^{125}$I radiolabeled Cry1Fa core toxin protein (0.5 nM) was incubated for 1 hr at 28° with O. nubilalis (ECB) BBMV proteins in concentrations ranging from 0 to 500 µg/mL in binding buffer (8 mM $NaHPO_4$, 2 mM $KH_2PO_4$, 150 mM NaCl, 0.1% BSA, pH7.4). Total volume was 0.5 mL. Bound $^{125}$I-Cry1Fa core toxin protein was separated from unbound material by sampling 150 µL of the reaction mixture in triplicate and centrifuging the samples at 14000×g for 8 min at room temperature. The supernatant was gently removed, and the pellet washed three times with ice cold binding buffer. The bottom of the centrifuge tube containing the pellet was cut off and placed into a 13×75-mm glass culture tube. Each sample was counted for 10 min in a gamma counter. The value of counts-per-minute (CPM) minus background (reactions with no added protein) was plotted versus BBMV protein concentration. The optimal range of BBMV protein to use in each binding reaction was determined to be 100 µg/mL to 150 µg/mL.

Binding kinetics: To determine the binding kinetics, a saturation curve was generated. Briefly, 150 µg/mL of ECB BBMV proteins were incubated for 1 hr at 28° with increasing concentrations (ranging from 0.5 nM to 20 nM) of $^{125}$I-Cry1Fa core toxin protein. Total binding was determined by sampling 150 µL of each concentration in triplicate, followed by centrifuging and counting as described above. The triplicate values were averaged. Non-specific binding was determined in the same manner, with the addition of 1,000 nM of non-radioactive (competitor) Cry1Fa core toxin protein. This concentration was at least 50-fold higher than the highest concentration of the radiolabeled Cry1Fa core toxin protein used; thus it would be expected to bind to all available receptor sites, while displacing the radiolabeled Cry1Fa core toxin protein. Specific binding was calculated as the difference in CPM (minus background) between total binding and non-specific binding. It was determined (FIG. 2) that $^{125}$I-Cry1Fa core toxin protein specifically bound to the ECB BBMV proteins in a saturable manner, with a $K_d$ of 11 nM and a $B_{max}$ of 37 fmoles/mg of ECB BBMV proteins. The level of non-specific binding was nearly 70% of total binding; however the level of specific binding clearly saturated, showing that the interaction was a receptor-mediated binding response.

EXAMPLE 7

Competition Binding Assays with BBMVs

A "pull-down" type receptor assay was used to determine the amount of competition for binding to receptor sites between radiolabeled Cry1Fa core toxin protein and other (non labeled) Cry toxin proteins. In this assay the relative molecular size of the bound ligand with receptor was characterized by separation by SDS-PAGE, and the amount of radiolabeled ligand bound to the BBMV receptor was measured by detection of radioactivity in the gel by phosphor-imaging. Homologous and heterologous competition binding assays were conducted using 100 µg/mL or 150 µg/mL of BBMV protein (from various insect sources) and 0.5 nM or 2.5 nM of $^{125}$I-Cry1Fa core toxin protein. The competitive ligand (i.e. 1000 nM of non-radiolabeled Cry toxin protein) was added to the reaction mixture at the same time as the radioactive ligand to assure true competitive binding interactions. Incubations were carried out for 1 hr at 28°, and the $^{125}$I-Cry1Fa core toxin protein bound to its BBMV receptor(s) was separated from nonbound protein by centrifuging the reaction mixture as described above. The pellet was washed three times with ice cold binding buffer, then solubilized by adding 25 µL of 2× Laemmli buffer with 5% β-mercaptoethanol, and rapidly mixing the sample for 10 min at 95°. The sample was centrifuged and duplicate samples were loaded onto a 4% to 20% Tris glycine polyacrylamide gel and separated by SDS-PAGE. The amount of $^{125}$I-Cry1Fa core toxin protein bound to receptor was measured by phosphor-imaging of the gel and densitometry of the bands corresponding to radioactive Cry1Fa core toxin protein after a 3 day exposure of the plate.

In a control reaction, 0.5 nM of $^{125}$I-Cry1Fa core toxin protein was incubated with *S. frugiperda* (FAW) BBMV proteins for 1 hr, and the amount of $^{125}$I-Cry1Fa protein that bound to the BBMVs was measured by SDS-PAGE and phosphor-imaging as above. A concurrent experiment, to which was added 1000 nM of unlabeled Cry1Fa core toxin protein, demonstrated that this addition of a 2000-fold excess concentration of unlabeled Cry1Fa core toxin protein completely eliminated the binding of the radiolabeled Cry1Fa protein. These results demonstrated that this assay effectively measures the ability of a Cry toxin protein to displace the binding of Cry1Fa core toxin protein to its FAW BBMV receptor(s). In a similar manner, it was determined that 1000 nM of Cry1Ab core toxin protein completely eliminated the binding of $^{125}$I-Cry1Fa core toxin protein to FAW BBMV proteins. This result is consistent with other reports indicating that the Cry1Ab toxin protein and Cry1Fa toxin protein share similar receptor binding sites (Banks et al., 2001; Hernandez and Ferre, 2005).

Further, it was found that there was no competition for binding to FAW BBMV receptors between 1000 nM of Cry1Ca core toxin protein and 0.5 nM of $^{125}$I-Cry1Fa core toxin protein, indicating that the Cry1Ca protein binds to a receptor different from the Cry1Fa receptor(s). This result is consistent with other studies conducted with *Diatraea saccharalis* (sugarcane borer) BBMVs, in which it was found that excess Cry1Fa protein did not displace biotinylated Cry1Ca protein from its receptor(s).

EXAMPLE 8

Cry1Fa Core Toxin Binding to BBMVs Prepared from FAW Insects Resistant to Cry1Fa Toxin Pull-down competitive binding assays were performed using BBMVs prepared from insect larvae that are resistant to intoxication by ingested Cry1Fa toxin. Cry1Fa-resistant larvae of *S. frugiperda* (rFAW)) were hatched from eggs harvested from a proprietary colony (Dow AgroSciences LLC, Indianapolis, Ind.). The rFAW larvae are more than 30-fold resistant to the toxicity of Cry1Fa toxin. BBMVs were prepared from rFAW larvae in the same manner as from their Cry1Fa-sensitive counterparts.

As shown above, BBMVs from wild type (i.e. Cry1Fa-sensitive) FAW larvae bound $^{125}$I-Cry1Fa, and the binding could be displaced by 2000-fold addition of non-labeled Cry1Fa protein. In contrast, BBMVs prepared from rFAW larvae and used in pull-down binding assays at 100 µg/mL with 2.5 nM $^{125}$I-Cry1Fa did not bind any of the $^{125}$I-Cry1Fa core toxin protein. These results indicate that the resistance to Cry1Fa toxin in rFAW may be due to the inability of the Cry1Fa receptor(s) in the BBMVs to bind Cry1Fa core toxin protein. Alternatively, the resistance may be a result of absence of the receptors from the insects. In any case, it appears that the mechanism of resistance to Cry1Fa toxin in these rFAW larvae is receptor based.

EXAMPLE 9

Cry1Fa Core Toxin Binding to BBMVs Prepared from ECB Insects Resistant to Cry1Fa Toxin Pull-down competitive binding assays were performed using BBMVs prepared from insect larvae that are resistant to intoxication by ingested Cry1Fa toxin. Cry1Fa-resistant larvae of *O. nubilalis* (rECB) were hatched from eggs harvested from a proprietary colony (Dow AgroSciences LLC, Indianapolis, Ind.). The rECB larvae are more than 30-fold resistant to the toxicity of Cry1Fa toxin. BBMVs were prepared from rECB larvae in the same manner as from their Cry1Fa-sensitive counterparts.

Pull-down experiments were conducted using 100 µg/mL of BBMVs prepared from wild type ECB larvae (i.e. Cry1Fa-sensitive) and Cry1Fa-resistant (rECB) larvae, and using 2.5 nM of $^{125}$I-Cry1Fa core toxin protein. The radioiodinated protein was bound to BBMVs from ECB larvae, but to a lesser extent than was seen for binding to BBMVs from FAW larvae. Non-radiolabeled (competitor) Cry1Fa protein competed with the binding of $^{125}$I-Cry1Fa to ECB BBMVs but the competition was less than that which was measured in competition experiments using FAW BBMVs.

Some binding of $^{125}$I-Cry1Fa to rECB BBMVs was detected, and the amount of binding was less than that measured using ECB BBMVs. Non-radiolabeled (competitor) Cry1Fa protein did not completely compete with $^{125}$I-Cry1Fa core toxin protein for binding to rECB BBMVs. These data support earlier Cry1Fa binding studies done by Surface Plasmon Resonance using BBMVs from ECB and rECB. Those studies showed that non-iodinated Cry1Fa toxin protein could bind to BBMV fractions prepared from either ECB or rECB larvae, but dissociation of the toxin from the ECB BBMVs was slower than its dissociation from rECB BBMVs. The $^{125}$I-Cry1Fa core toxin protein binding detected in the pull-down type assays described here are not sufficiently quantitative to measure binding affinity, but do indicate that Cry1Fa toxin protein binds to rECB BBMVs to a significant degree. Thus, resistance to Cry1Fa toxin in rECB may be due to less efficient binding of Cry1Fa core toxin protein to rECB BBMV receptor(s), as compared to binding to receptors of susceptible larvae. This could manifest as less efficacious for membrane pore formation, since the time that the toxin remains on the receptor is shorter than in susceptible insects.

Table 1 summarizes the relative binding results from assays using radio-iodinated Cry1Fa core toxin protein with BBMV preparations from various insect sources. Percentages indicate the relative amounts of radioactivity bound to BBMVs, with, and without, nonradioactive competitor ligand. 100% values do not represent equal numbers; ECB BBMVs bind less total Cry1Fa protein than do FAW BBMVs.

TABLE 1

| | Relative Amounts of radio-iodinated Cry1Fa Protein Bound Non labeled Competitor* | | | |
|---|---|---|---|---|
| | None | Cry1Fa | Cry1Ab | Cry1Ca |
| FAW BBMVs | 100% | 0% | −4% | 50% |
| rFAW BBMVs | 10% | NA** | Not done | Not done |
| ECB BBMVs | 100% | 31% | Not done | Not done |
| rECB BBMVs | 64% | 51% | Not done | Not done |

*1000 nM of nonradioactive competitor Cry core toxin proteins added where appropriate
**N/A = Not Applicable, since very little $^{125}$I-Cry1Fa core toxin protein was bound This invention demonstrates that, surprisingly, Cry1Fa core toxin protein can be radio-labeled using $^{125}$I labeled fluorescein-5-maleimide to specifically alkylate cysteine residues while maintaining insecticidal activity and receptor binding capability. The trypsin truncated form of Cry1Fa core toxin contains only a single cysteine residue (corresponding to C205 within Domain I of Cry1Fa), which must comprise the site of radiolabeling. This region constitutes part of the pore structure of the protein and is not thought to be involved in receptor binding. One skilled in the field of protein biochemistry and structure will realize that molecules similar to fluorescein-5-maleimide, which contain a phenol ring attached to a maleimide function, could be iodinated by chloramine chemistry and could be used to iodinate specific cysteine residues in proteins such as Cry1Fa. In particular, analogs smaller than fluorescein-5-maleimide might be more accessible to the interior of Cry1Fa core toxin thus may result in greater specific radioactivity of the labeled protein.

The cysteine alkylated Cry1Fa protein produced herein is insecticidally active against FAW larvae. Unlabeled Cry1Fa protein and unlabeled Cry1Ab protein, but not unlabeled Cry1Ca protein, can displace the binding of radiolabeled Cry1Fa protein from FAW BBMVs. Bioassay data demonstrates that Cry1Ca is active against both FAW and rFAW larvae, while Cry1Ab is less active against rFAW larvae. Thus, the biological activities of Cry1Fa, Cry1Ab, and Cry1Ca proteins against FAW and rFAW larvae are conveniently explained and predicted by the BBMV binding assay results. It is therefore one aspect of this invention that combinations of Cry proteins useful in Insect Management strategies may be predicted using competitive binding assays employing Cry1Fa protein radiolabeled by means of the methods of this invention.

REFERENCES

Ausubel et al., eds. (1995) Current Protocols in Molecular Biology, Chapter 2 (Greene Publishing and Wiley-Interscience, New York).

Ballester, V., Granero, F., de Maagd, R. A., Bosch, D., Mensua, J. L., and Ferre, J. (1999) Role of *Bacillus thuringiensis* Toxin Domains in Toxicity and Receptor Binding in the Diamondback Moth. Appl. Environ. Microbiol. 65:1900-1903.

Banks, D. J., Jurat-Fuentes, J. L., Dean, D. H., and Adang, M. J. (2001) *Bacillus thuringiensis* Cry1Ac and Cry1Fa delta-endotoxin binding to a novel 110 kDa aminopeptidase in *Heliothis virescens* is not N-acetylgalactosamine mediated. Insect Biochem. Mol. Biol. 31:909-918.

Bernardi, R., Tedeschi, G., Ronchi, S., and Palmieri, S. (1996) Isolation and some molecular properties of a trypsin-like enzyme from larvae of European corn borer *Ostrinia nubilalis* Hubner (Lepidoptera: pyralidae). Insect Biochem. Molec. Biol. 26:883-889.

Bradford, M. M. (1976) A rapid and sensitive method for the quantitation of microgram quantities of protein utilizing the principle of protein-dye binding. Anal. Biochem. 72, 248-254.

Bravo, A., Gill, S. S., and Soberon, M. (2007) Mode of action of *Bacillus thuringiensis* Cry and Cyt toxins and their potential for insect control. Toxicon. 49:423-435.

Christeller, J. T., Laing, W. A., Marwick, N. P., and Burgess, E. P. J. (1992) Midgut protease activities in 12 phytophagous lepidopteran larvae: Dietary and protease inhibitor interactions. Insect Biochem. Molec. Biol. 22:735-746.

Crickmore, N., Zeigler, D. R., Feitelson, J., Schnepf, E., Van Rie, J., Lereclus, D., Baum, J., and Dean, D. H. (1998) Revision of the nomenclature for the *Bacillus thuringiensis* pesticidal crystal proteins. Microbiol. Molec. Biol. Rev. 62:807-813.

de Maagd, R. A., Bakker, P. L., Masson, L., Adang, M. J., Sangadala, S., Stiekema, W., and Bosch, D. (1999) Domain III of the *Bacillus thuringiensis* delta-endotoxin Cry1Ac is involved in binding to *Manduca sexta* brush border membranes and to its purified aminopeptidase N. Molec. Microbiol. 31:463-471.

de Maagd, R. A., Bravo, A., Berry, C., Crickmore, N., and Schnepf, H. E. (2003) Structure, diversity, and evolution of protein toxins from spore-forming entomopathogenic bacteria. Annu. Rev. Genet. 37:409-433.

de Maagd, R. A., Kwa, M. S., van der Klei, H., Yamamoto, T., Schipper, B., Vlak, J. M., Stiekema, W. J., and Bosch, D. (1996) Domain III substitution in *Bacillus thuringiensis* delta-endotoxin CryIA(b) results in superior toxicity for *Spodoptera exigua* and altered membrane protein recognition. Appl. Environ. Microbiol. 62:1537-1543.

Gatehouse, L. N., Shannon, A. L., Burgess, E. P., and Christeller, J. T. (1997) Characterization of major midgut proteinase cDNAs from *Helicoverpa armigera* larvae and changes in gene expression in response to four proteinase inhibitors in the diet. Insect Biochem. Molec. Biol. 27:929-944.

Gomez, I., Arenas, I., Benitez, I., Miranda-Rios, J., Becerril, B., Grande, R., Almagro, J. C., Bravo, A., and Soberon, M. (2006) Specific epitopes of domains II and III of *Bacillus thuringiensis* Cry1Ab toxin involved in the sequential interaction with cadherin and aminopeptidase-N receptors in *Manduca sexta*. J. Biol. Chem. 281:34032-34039.

Gomez, I., Dean, D. H., Bravo, A., and Soberon, M. (2003) Molecular basis for *Bacillus thuringiensis* Cry1Ab toxin specificity: two structural determinants in the *Manduca sexta* Bt-R1 receptor interact with loops alpha-8 and 2 in domain II of Cry1Ab toxin. Biochem. 42:10482-10489.

Gomez, I., Pardo-Lopez, L., Munoz-Garay, C., Fernandez, L. E., Perez, C., Sanchez, J., Soberon, M., and Bravo, A. (2007) Role of receptor interaction in the mode of action of insecticidal Cry and Cyt toxins produced by *Bacillus thuringiensis*. Peptides 28:169-173.

Griffitts, J. S. and Aroian, R. V. (2005) Many roads to resistance: how invertebrates adapt to Bt toxins. Bioessays 27:614-624.

Heckel, D. G., Gahan, L. J., Baxter, S. W., Zhao, J. Z., Shelton, A. M., Gould, F., and Tabashnik, B. E. (2007) The diversity of Bt resistance genes in species of Lepidoptera. J. Invert. Pathol. 95:192-197.

Hernandez, C. S. and Ferre, J. (2005) Common receptor for *Bacillus thuringiensis* toxins Cry1Ac, Cry1Fa, and Cry1Ja in *Helicoverpa armigera, Helicoverpa zea,* and *Spodoptera exigua*. Appl. Environ. Microbiol. 71:5627-5629.

Herrero, S., Gonzalez-Cabrera, J., Ferre, J., Bakker, P. L., and de Maagd, R. A. (2004) Mutations in the *Bacillus thuringiensis* Cry1Ca toxin demonstrate the role of domains II and III in specificity towards *Spodoptera exigua* larvae. Biochem. J. 384:507-513.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Lee, M. K., You, T. H., Gould, F. L., and Dean, D. H. (1999) Identification of residues in domain III of *Bacillus thuringiensis* Cry1Ac toxin that affect binding and toxicity. Appl. Environ. Microbiol. 65:4513-4520.

Luo, K., Banks, D., and Adang, M. J. (1999) Toxicity, binding, and permeability analyses of four *Bacillus thuringiensis* Cry1 delta-endotoxins using brush border membrane vesicles of *Spodoptera exigua* and *Spodoptera frugiperda*. Appl. Environ. Microbiol. 65:457-464.

Palmer, M., Buchkremer, M, Valeva, A, and Bhakdi, S. (1997) Cysteine-specific radioiodination of proteins with fluorescein maleimide. Anal. Biochem. 253:175-179.

Pigott, C. R. and Ellar, D. J. (2007) Role of receptors in *Bacillus thuringiensis* crystal toxin activity. Microbiol. Molec. Biol. Rev. 71:255-281.

Rausell, C., Garcia-Robles, I., Sanchez, J., Munoz-Garay, C., Martinez-Ramirez, A. C., Real, M. D., and Bravo, A. (2004) Role of toxin activation on binding and pore formation activity of the *Bacillus thuringiensis* Cry3 toxins in membranes of *Leptinotarsa decemlineata* (Say). Biochim. Biophys. Acta 1660:99-105.

Sambrook, J., Fritsch, E. F., Maniatis, T. (1989) Molecular Cloning: A Laboratory Manual (2nd ed., Cold Spring Harbor Laboratory Press, Plainview, N.Y.)

Squires, C. H., Retallack, D. M., Chew, L. C., Ramseier, T. M., Schneider, J. C., Talbot, H. W. (2004) Heterologous protein production in *P. fluorescens*. Bioprocess Intern. 2:54-59.

Van Rie, J., Jansens, S., Hofte, H., Degheele, D., and Van Mellaert, H. (1990a) Receptors on the brush border membrane of the insect midgut as determinants of the specificity of *Bacillus thuringiensis* delta-endotoxins. Appl. Environ. Microbiol. 56:1378-1385.

Van Rie, J., McGaughey, W. H., Johnson, D. E., Barnett, B. D., and Van Mellaert, H. (1990b) Mechanism of insect resistance to the microbial insecticide *Bacillus thuringiensis*. Science 247:72-74.

Wolfersberger, M. G. (1993) Preparation and partial characterization of amino acid transporting brush border membrane vesicles from the larval midgut of the gypsy moth (*Lymantria dispar*). Arch. Insect Biochem. Physiol 24:139-147.

We claim:

1. A Cry1Fa holotoxin labeled with radioiodinated fluorescein-5-maleimide at position C205, said radiolabeled holotoxin retaining the ability to selectively bind to receptors in brush border membrane vesicles prepared from midguts of *Spodoptera exigua* and *Spodoptera frugiperda*.

2. The Cry1Fa holotoxin of claim 1, said radiolabeled Cry1Fa holotoxin having insecticidal activity.

* * * * *

SEQUENCE LISTING

```
<160> NUMBER OF SEQ ID NOS: 2

<210> SEQ ID NO 1
<211> LENGTH: 3447
<212> TYPE: DNA
<213> ORGANISM: Artificial Sequence
<220> FEATURE:
<223> OTHER INFORMATION: Synthetic plant optimized coding region
      encoding chimeric Cry
      protein
<220> FEATURE:
<221> NAME/KEY: CDS
<222> LOCATION: (1)..(3444)

<400> SEQUENCE: 1 atg gaa aat aat att caa aat caa tgc gta cct tac aat tgt tta aat       48
Met Glu Asn Asn Ile Gln Asn Gln Cys Val Pro Tyr Asn Cys Leu Asn
```

```
        1               5                   10                  15
aat cct gaa gta gaa ata ctg aac gaa gaa cgc agc acc ggc cgc ctg        96
Asn Pro Glu Val Glu Ile Leu Asn Glu Glu Arg Ser Thr Gly Arg Leu
             20                  25                  30 ccg ctg gac atc agc ctg agc ctt aca cgt ttc ctt ttg agt gaa ttt       144
Pro Leu Asp Ile Ser Leu Ser Leu Thr Arg Phe Leu Leu Ser Glu Phe
                 35                  40                  45 gtt cca ggt gtg gga gtt gcg ttt gga tta ttt gat tta ata tgg ggt       192
Val Pro Gly Val Gly Val Ala Phe Gly Leu Phe Asp Leu Ile Trp Gly
         50                  55                  60 ttt ata act cct tct gat tgg agc tta ttt ctt tta cag att gaa caa       240
Phe Ile Thr Pro Ser Asp Trp Ser Leu Phe Leu Leu Gln Ile Glu Gln
65                  70                  75                  80 ttg att gag caa aga ata gaa aca ttg gaa agg aac cgg gca att act       288
Leu Ile Glu Gln Arg Ile Glu Thr Leu Glu Arg Asn Arg Ala Ile Thr
                 85                  90                  95 aca tta cga ggg tta gca gat agc tat gaa att tat att gaa gca cta       336
Thr Leu Arg Gly Leu Ala Asp Ser Tyr Glu Ile Tyr Ile Glu Ala Leu
             100                 105                 110 aga gag tgg gaa gca aat cct aat aat gca caa tta agg gaa gat gtg       384
Arg Glu Trp Glu Ala Asn Pro Asn Asn Ala Gln Leu Arg Glu Asp Val
         115                 120                 125 cgt att cga ttt gct aat aca gac gac gct tta ata aca gca ata aat       432
Arg Ile Arg Phe Ala Asn Thr Asp Asp Ala Leu Ile Thr Ala Ile Asn
     130                 135                 140 aat ttt aca ctt aca agt ttt gaa atc cct ctt tta tcg gtc tat gtt       480
Asn Phe Thr Leu Thr Ser Phe Glu Ile Pro Leu Leu Ser Val Tyr Val
145                 150                 155                 160 caa gcg gcg aat tta cat tta tca cta tta aga gac gca gta tcg ttt       528
Gln Ala Ala Asn Leu His Leu Ser Leu Leu Arg Asp Ala Val Ser Phe
                 165                 170                 175 ggg cag ggt tgg gga ctg gat ata gct act gtt aat aat cat tat aat       576
Gly Gln Gly Trp Gly Leu Asp Ile Ala Thr Val Asn Asn His Tyr Asn
             180                 185                 190 aga tta ata aat ctt att cat aga tat acg aaa cat tgt ttg gac aca       624
Arg Leu Ile Asn Leu Ile His Arg Tyr Thr Lys His Cys Leu Asp Thr
         195                 200                 205 tac aat caa gga tta gaa aac tta aga ggt act aat act cga caa tgg       672
Tyr Asn Gln Gly Leu Glu Asn Leu Arg Gly Thr Asn Thr Arg Gln Trp
     210                 215                 220 gca aga ttc aat cag ttt agg aga gat tta aca ctt act gta tta gat       720
Ala Arg Phe Asn Gln Phe Arg Arg Asp Leu Thr Leu Thr Val Leu Asp
225                 230                 235                 240 atc gtt gct ctt ttt ccg aac tac gat gtt aga aca tat cca att caa       768
Ile Val Ala Leu Phe Pro Asn Tyr Asp Val Arg Thr Tyr Pro Ile Gln
                 245                 250                 255 acg tca tcc caa tta aca agg gaa att tat aca agt tca gta att gag       816
Thr Ser Ser Gln Leu Thr Arg Glu Ile Tyr Thr Ser Ser Val Ile Glu
             260                 265                 270 gat tct cca gtt tct gct aat ata cct aat ggt ttt aat agg gcg gaa       864
Asp Ser Pro Val Ser Ala Asn Ile Pro Asn Gly Phe Asn Arg Ala Glu
         275                 280                 285 ttt gga gtt aga ccg ccc cat ctt atg gac ttt atg aat tct ttg ttt       912
Phe Gly Val Arg Pro Pro His Leu Met Asp Phe Met Asn Ser Leu Phe
     290                 295                 300 gta act gca gag act gtt aga agt caa act gtg tgg gga gga cac tta       960
Val Thr Ala Glu Thr Val Arg Ser Gln Thr Val Trp Gly Gly His Leu
305                 310                 315                 320 gtt agt tca cga aat acg gct ggt aac cgt ata aat ttc cct agt tac      1008
```

-continued

```
                Val Ser Ser Arg Asn Thr Ala Gly Asn Arg Ile Asn Phe Pro Ser Tyr
                                325                 330                 335 ggg gtc ttc aat cct ggt ggc gcc att tgg att gca gat gag gat cca          1056
Gly Val Phe Asn Pro Gly Gly Ala Ile Trp Ile Ala Asp Glu Asp Pro
            340                 345                 350 cgt cct ttt tat cgg aca tta tca gat cct gtt ttt gtc cga gga gga          1104
Arg Pro Phe Tyr Arg Thr Leu Ser Asp Pro Val Phe Val Arg Gly Gly
        355                 360                 365 ttt ggg aat cct cat tat gta ctg ggg ctt agg gga gta gca ttt caa          1152
Phe Gly Asn Pro His Tyr Val Leu Gly Leu Arg Gly Val Ala Phe Gln
    370                 375                 380 caa act ggt acg aac cac acc cga aca ttt aga aat agt ggg acc ata          1200
Gln Thr Gly Thr Asn His Thr Arg Thr Phe Arg Asn Ser Gly Thr Ile
385                 390                 395                 400 gat tct cta gat gaa atc cca cct cag gat aat agt ggg gca cct tgg          1248
Asp Ser Leu Asp Glu Ile Pro Pro Gln Asp Asn Ser Gly Ala Pro Trp
                405                 410                 415 aat gat tat agt cat gta tta aat cat gtt aca ttt gta cga tgg cca          1296
Asn Asp Tyr Ser His Val Leu Asn His Val Thr Phe Val Arg Trp Pro
            420                 425                 430 ggt gag att tca gga agt gat tca tgg aga gct cca atg ttt tct tgg          1344
Gly Glu Ile Ser Gly Ser Asp Ser Trp Arg Ala Pro Met Phe Ser Trp
        435                 440                 445 acg cac cgt agt gca acc cct aca aat aca att gat ccg gag agg att          1392
Thr His Arg Ser Ala Thr Pro Thr Asn Thr Ile Asp Pro Glu Arg Ile
    450                 455                 460 act caa ata cca ttg gta aaa gca cat aca ctt cag tca ggt act act          1440
Thr Gln Ile Pro Leu Val Lys Ala His Thr Leu Gln Ser Gly Thr Thr
465                 470                 475                 480 gtt gta aga ggg ccc ggg ttt acg gga gga gat att ctt cga cga aca          1488
Val Val Arg Gly Pro Gly Phe Thr Gly Gly Asp Ile Leu Arg Arg Thr
                485                 490                 495 agt gga gga cca ttt gct tat act att gtt aat ata aat ggg caa tta          1536
Ser Gly Gly Pro Phe Ala Tyr Thr Ile Val Asn Ile Asn Gly Gln Leu
            500                 505                 510 ccc caa agg tat cgt gca aga ata cgc tat gcc tct act aca aat cta          1584
Pro Gln Arg Tyr Arg Ala Arg Ile Arg Tyr Ala Ser Thr Thr Asn Leu
        515                 520                 525 aga att tac gta acg gtt gca ggt gaa cgg att ttt gct ggt caa ttt          1632
Arg Ile Tyr Val Thr Val Ala Gly Glu Arg Ile Phe Ala Gly Gln Phe
    530                 535                 540 aac aaa aca atg gat acc ggt gac cca tta aca ttc caa tct ttt agt          1680
Asn Lys Thr Met Asp Thr Gly Asp Pro Leu Thr Phe Gln Ser Phe Ser
545                 550                 555                 560 tac gca act att aat aca gct ttt aca ttc cca atg agc cag agt agt          1728
Tyr Ala Thr Ile Asn Thr Ala Phe Thr Phe Pro Met Ser Gln Ser Ser
                565                 570                 575 ttc aca gta ggt gct gat act ttt agt tca ggg aat gaa gtt tat ata          1776
Phe Thr Val Gly Ala Asp Thr Phe Ser Ser Gly Asn Glu Val Tyr Ile
            580                 585                 590 gac aga ttt gaa ttg att cca gtt act gca aca ttg gaa gca gaa tct          1824
Asp Arg Phe Glu Leu Ile Pro Val Thr Ala Thr Leu Glu Ala Glu Ser
        595                 600                 605 gat tta gaa aga gca caa aag gcg gtg aat gcg ctg ttt act tct agc          1872
Asp Leu Glu Arg Ala Gln Lys Ala Val Asn Ala Leu Phe Thr Ser Ser
    610                 615                 620 aac caa ata ggg cta aaa aca gat gtg acg gat tat cat atc gat cga          1920
Asn Gln Ile Gly Leu Lys Thr Asp Val Thr Asp Tyr His Ile Asp Arg
625                 630                 635                 640
```

-continued

| | | |
|---|---|---|
| gta tcc aat tta gtt gag tgt tta tct gat gaa ttt tgt ctg gat gaa<br>Val Ser Asn Leu Val Glu Cys Leu Ser Asp Glu Phe Cys Leu Asp Glu<br>                645                     650                  655 | 1968 | |
| aaa aaa gaa ttg tcc gag aaa gtc aaa cat gcg aag cga ctt agt gat<br>Lys Lys Glu Leu Ser Glu Lys Val Lys His Ala Lys Arg Leu Ser Asp<br>                660                     665                  670 | 2016 | |
| gag cgg aat tta ctt caa gat cca aac ttt aga ggg atc aat aga caa<br>Glu Arg Asn Leu Leu Gln Asp Pro Asn Phe Arg Gly Ile Asn Arg Gln<br>        675                     680                     685 | 2064 | |
| cta gac cgt ggc tgg aga gga agt acg gat att acc atc caa gga ggc<br>Leu Asp Arg Gly Trp Arg Gly Ser Thr Asp Ile Thr Ile Gln Gly Gly<br>690                     695                     700 | 2112 | |
| gat gac gta ttc aaa gag aat tac gtt acg cta ttg ggt acc ttt gat<br>Asp Asp Val Phe Lys Glu Asn Tyr Val Thr Leu Leu Gly Thr Phe Asp<br>705                    710                     715                  720 | 2160 | |
| gag tgc tat cca acg tat tta tat caa aaa ata gat gag tcg aaa tta<br>Glu Cys Tyr Pro Thr Tyr Leu Tyr Gln Lys Ile Asp Glu Ser Lys Leu<br>                      725                     730                  735 | 2208 | |
| aaa gcc tat acc cgt tac caa tta aga ggg tat atc gaa gat agt caa<br>Lys Ala Tyr Thr Arg Tyr Gln Leu Arg Gly Tyr Ile Glu Asp Ser Gln<br>                740                     745                     750 | 2256 | |
| gac tta gaa atc tat tta att cgc tac aat gcc aaa cac gaa aca gta<br>Asp Leu Glu Ile Tyr Leu Ile Arg Tyr Asn Ala Lys His Glu Thr Val<br>                      755                     760                  765 | 2304 | |
| aat gtg cca ggt acg ggt tcc tta tgg ccg ctt tca gcc cca agt cca<br>Asn Val Pro Gly Thr Gly Ser Leu Trp Pro Leu Ser Ala Pro Ser Pro<br>770                     775                     780 | 2352 | |
| atc gga aaa tgt gcc cat cat tcc cat cat ttc tcc ttg gac att gat<br>Ile Gly Lys Cys Ala His His Ser His His Phe Ser Leu Asp Ile Asp<br>785                    790                     795                  800 | 2400 | |
| gtt gga tgt aca gac tta aat gag gac tta ggt gta tgg gta ata ttc<br>Val Gly Cys Thr Asp Leu Asn Glu Asp Leu Gly Val Trp Val Ile Phe<br>                     805                     810                  815 | 2448 | |
| aag att aag acg caa gat ggc cat gca aga cta gga aat cta gaa ttt<br>Lys Ile Lys Thr Gln Asp Gly His Ala Arg Leu Gly Asn Leu Glu Phe<br>              820                     825                  830 | 2496 | |
| ctc gaa gag aaa cca tta gta gga gaa gca cta gct cgt gtg aaa aga<br>Leu Glu Glu Lys Pro Leu Val Gly Glu Ala Leu Ala Arg Val Lys Arg<br>        835                     840                     845 | 2544 | |
| gcg gag aaa aaa tgg aga gac aaa cgt gaa aaa ttg gaa tgg gaa aca<br>Ala Glu Lys Lys Trp Arg Asp Lys Arg Glu Lys Leu Glu Trp Glu Thr<br>850                     855                     860 | 2592 | |
| aat att gtt tat aaa gag gca aaa gaa tct gta gat gct tta ttt gta<br>Asn Ile Val Tyr Lys Glu Ala Lys Glu Ser Val Asp Ala Leu Phe Val<br>865                    870                     875                  880 | 2640 | |
| aac tct caa tat gat aga tta caa gcg gat acc aac atc gcg atg att<br>Asn Ser Gln Tyr Asp Arg Leu Gln Ala Asp Thr Asn Ile Ala Met Ile<br>                      885                     890                  895 | 2688 | |
| cat gcg gca gat aaa cgc gtt cat agc att cga gaa gct tat ctg cct<br>His Ala Ala Asp Lys Arg Val His Ser Ile Arg Glu Ala Tyr Leu Pro<br>              900                     905                  910 | 2736 | |
| gag ctg tct gtg att ccg ggt gtc aat gcg gct att ttt gaa gaa tta<br>Glu Leu Ser Val Ile Pro Gly Val Asn Ala Ala Ile Phe Glu Glu Leu<br>        915                     920                     925 | 2784 | |
| gaa ggg cgt att ttc act gca ttc tcc cta tat gat gcg aga aat gtc<br>Glu Gly Arg Ile Phe Thr Ala Phe Ser Leu Tyr Asp Ala Arg Asn Val<br>930                     935                     940 | 2832 | |
| att aaa aat ggt gat ttt aat aat ggc tta tcc tgc tgg aac gtg aaa<br>Ile Lys Asn Gly Asp Phe Asn Asn Gly Leu Ser Cys Trp Asn Val Lys<br>945                      950                     955                  960 | 2880 | |

```
ggg cat gta gat gta gaa gaa caa aac aac cac cgt tcg gtc ctt gtt         2928
Gly His Val Asp Val Glu Glu Gln Asn Asn His Arg Ser Val Leu Val
            965                 970                 975 gtt ccg gaa tgg gaa gca gaa gtg tca caa gaa gtt cgt gtc tgt ccg         2976
Val Pro Glu Trp Glu Ala Glu Val Ser Gln Glu Val Arg Val Cys Pro
        980                 985                 990 ggt cgt ggc tat atc ctt cgt gtc aca gcg tac aag gag gga tat gga         3024
Gly Arg Gly Tyr Ile Leu Arg Val Thr Ala Tyr Lys Glu Gly Tyr Gly
        995                1000                1005 gaa ggt tgc gta acc att cat gag atc gag aac aat aca gac gaa             3069
Glu Gly Cys Val Thr Ile His Glu Ile Glu Asn Asn Thr Asp Glu
    1010                1015                1020 ctg aag ttt agc aac tgt gta gaa gag gaa gta tat cca aac aac             3114
Leu Lys Phe Ser Asn Cys Val Glu Glu Glu Val Tyr Pro Asn Asn
    1025                1030                1035 acg gta acg tgt aat gat tat act gcg act caa gaa gaa tat gag             3159
Thr Val Thr Cys Asn Asp Tyr Thr Ala Thr Gln Glu Glu Tyr Glu
    1040                1045                1050 ggt acg tac act tct cgt aat cga gga tat gac gga gcc tat gaa             3204
Gly Thr Tyr Thr Ser Arg Asn Arg Gly Tyr Asp Gly Ala Tyr Glu
    1055                1060                1065 agc aat tct tct gta cca gct gat tat gca tca gcc tat gaa gaa             3249
Ser Asn Ser Ser Val Pro Ala Asp Tyr Ala Ser Ala Tyr Glu Glu
    1070                1075                1080 aaa gca tat aca gat gga cga aga gac aat cct tgt gaa tct aac             3294
Lys Ala Tyr Thr Asp Gly Arg Arg Asp Asn Pro Cys Glu Ser Asn
    1085                1090                1095 aga gga tat ggg gat tac aca cca cta cca gct ggc tat gtg aca             3339
Arg Gly Tyr Gly Asp Tyr Thr Pro Leu Pro Ala Gly Tyr Val Thr
    1100                1105                1110 aaa gaa tta gag tac ttc cca gaa acc gat aag gta tgg att gag             3384
Lys Glu Leu Glu Tyr Phe Pro Glu Thr Asp Lys Val Trp Ile Glu
    1115                1120                1125 atc gga gaa acg gaa gga aca ttc atc gtg gac agc gtg gaa tta             3429
Ile Gly Glu Thr Glu Gly Thr Phe Ile Val Asp Ser Val Glu Leu
    1130                1135                1140 ctt ctt atg gag gaa taa                                                 3447
Leu Leu Met Glu Glu
    1145

<210> SEQ ID NO 2
<211> LENGTH: 1148
<212> TYPE: PRT
<213> ORGANISM: Artificial Sequence
<220> FEATURE:
<223> OTHER INFORMATION: Synthetic Construct

<400> SEQUENCE: 2

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
```

```
            85                  90                  95
Thr Leu Arg Gly Leu Ala Asp Ser Tyr Glu Ile Tyr Ile Glu Ala Leu
            100                 105                 110
Arg Glu Trp Glu Ala Asn Pro Asn Asn Ala Gln Leu Arg Glu Asp Val
            115                 120                 125
Arg Ile Arg Phe Ala Asn Thr Asp Asp Ala Leu Ile Thr Ala Ile Asn
            130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
                180                 185                 190
Arg Leu Ile Asn Leu Ile His Arg Tyr Thr Lys His Cys Leu Asp Thr
                195                 200                 205
Tyr Asn Gln Gly Leu Glu Asn Leu Arg Gly Thr Asn Thr Arg Gln Trp
            210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
            260                 265                 270
Asp Ser Pro Val Ser Ala Asn Ile Pro Asn Gly Phe Asn Arg Ala Glu
            275                 280                 285
Phe Gly Val Arg Pro Pro His Leu Met Asp Phe Met Asn Ser Leu Phe
290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
            355                 360                 365
Phe Gly Asn Pro His Tyr Val Leu Gly Leu Arg Gly Val Ala Phe Gln
            370                 375                 380
Gln Thr Gly Thr Asn His Thr Arg Thr Phe Arg Asn Ser Gly Thr Ile
385                 390                 395                 400
Asp Ser Leu Asp Glu Ile Pro Pro Gln Asp Asn Ser Gly Ala Pro Trp
                405                 410                 415
Asn Asp Tyr Ser His Val Leu Asn His Val Thr Phe Val Arg Trp Pro
            420                 425                 430
Gly Glu Ile Ser Gly Ser Asp Ser Trp Arg Ala Pro Met Phe Ser Trp
            435                 440                 445
Thr His Arg Ser Ala Thr Pro Thr Asn Thr Ile Asp Pro Glu Arg Ile
450                 455                 460
Thr Gln Ile Pro Leu Val Lys Ala His Thr Leu Gln Ser Gly Thr Thr
465                 470                 475                 480
Val Val Arg Gly Pro Gly Phe Thr Gly Gly Asp Ile Leu Arg Arg Thr
            485                 490                 495
Ser Gly Gly Pro Phe Ala Tyr Thr Ile Val Asn Ile Asn Gly Gln Leu
            500                 505                 510
```

```
Pro Gln Arg Tyr Arg Ala Arg Ile Arg Tyr Ala Ser Thr Thr Asn Leu
    515                 520                 525

Arg Ile Tyr Val Thr Val Ala Gly Glu Arg Ile Phe Ala Gly Gln Phe
530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
                580                 585                 590

Asp Arg Phe Glu Leu Ile Pro Val Thr Ala Thr Leu Glu Ala Glu Ser
    595                 600                 605

Asp Leu Glu Arg Ala Gln Lys Ala Val Asn Ala Leu Phe Thr Ser Ser
    610                 615                 620

Asn Gln Ile Gly Leu Lys Thr Asp Val Thr Asp Tyr His Ile Asp Arg
625                 630                 635                 640

Val Ser Asn Leu Val Glu Cys Leu Ser Asp Glu Phe Cys Leu Asp Glu
                645                 650                 655

Lys Lys Glu Leu Ser Lys Val Lys His Ala Lys Arg Leu Ser Asp
                660                 665                 670

Glu Arg Asn Leu Leu Gln Asp Pro Asn Phe Arg Gly Ile Asn Arg Gln
            675                 680                 685

Leu Asp Arg Gly Trp Arg Gly Ser Thr Asp Ile Thr Ile Gln Gly Gly
    690                 695                 700

Asp Asp Val Phe Lys Glu Asn Tyr Val Thr Leu Leu Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Tyr Thr Arg Tyr Gln Leu Arg Gly Tyr Ile Glu Asp Ser Gln
                740                 745                 750

Asp Leu Glu Ile Tyr Leu Ile Arg Tyr Asn Ala Lys His Glu Thr Val
    755                 760                 765

Asn Val Pro Gly Thr Gly Ser Leu Trp Pro Leu Ser Ala Pro Ser Pro
    770                 775                 780

Ile Gly Lys Cys Ala His His Ser His His Phe Ser Leu Asp Ile Asp
785                 790                 795                 800

Val Gly Cys Thr Asp Leu Asn Glu Asp Leu Gly Val Trp Val Ile Phe
                805                 810                 815

Lys Ile Lys Thr Gln Asp Gly His Ala Arg Leu Gly Asn Leu Glu Phe
                820                 825                 830

Leu Glu Glu Lys Pro Leu Val Gly Glu Ala Leu Ala Arg Val Lys Arg
            835                 840                 845

Ala Glu Lys Lys Trp Arg Asp Lys Arg Glu Lys Leu Glu Trp Glu Thr
850                 855                 860

Asn Ile Val Tyr Lys Glu Ala Lys Glu Ser Val Asp Ala Leu Phe Val
865                 870                 875                 880

Asn Ser Gln Tyr Asp Arg Leu Gln Ala Asp Thr Asn Ile Ala Met Ile
                885                 890                 895

His Ala Ala Asp Lys Arg Val His Ser Ile Arg Glu Ala Tyr Leu Pro
            900                 905                 910

Glu Leu Ser Val Ile Pro Gly Val Asn Ala Ala Ile Phe Glu Glu Leu
            915                 920                 925
```

```
Glu Gly Arg Ile Phe Thr Ala Phe Ser Leu Tyr Asp Ala Arg Asn Val
    930                 935                 940

Ile Lys Asn Gly Asp Phe Asn Asn Gly Leu Ser Cys Trp Asn Val Lys
945                 950                 955                 960

Gly His Val Asp Val Glu Glu Gln Asn Asn His Arg Ser Val Leu Val
                965                 970                 975

Val Pro Glu Trp Glu Ala Glu Val Ser Gln Glu Val Arg Val Cys Pro
                980                 985                 990

Gly Arg Gly Tyr Ile Leu Arg Val Thr Ala Tyr Lys Glu Gly Tyr Gly
        995                 1000                1005

Glu Gly Cys Val Thr Ile His Glu Ile Glu Asn Asn Thr Asp Glu
    1010                1015                1020

Leu Lys Phe Ser Asn Cys Val Glu Glu Glu Val Tyr Pro Asn Asn
    1025                1030                1035

Thr Val Thr Cys Asn Asp Tyr Thr Ala Thr Gln Glu Glu Tyr Glu
    1040                1045                1050

Gly Thr Tyr Thr Ser Arg Asn Arg Gly Tyr Asp Gly Ala Tyr Glu
    1055                1060                1065

Ser Asn Ser Ser Val Pro Ala Asp Tyr Ala Ser Ala Tyr Glu Glu
    1070                1075                1080

Lys Ala Tyr Thr Asp Gly Arg Arg Asp Asn Pro Cys Glu Ser Asn
    1085                1090                1095

Arg Gly Tyr Gly Asp Tyr Thr Pro Leu Pro Ala Gly Tyr Val Thr
    1100                1105                1110

Lys Glu Leu Glu Tyr Phe Pro Glu Thr Asp Lys Val Trp Ile Glu
    1115                1120                1125

Ile Gly Glu Thr Glu Gly Thr Phe Ile Val Asp Ser Val Glu Leu
    1130                1135                1140

Leu Leu Met Glu Glu
    1145
```